United States Patent [19]
Hawkins et al.

[11] Patent Number: 5,981,232
[45] Date of Patent: Nov. 9, 1999

[54] HUMAN PYROPHOSPHATASE

[75] Inventors: Phillip R. Hawkins, Mountain View; Jennifer L. Hillman, San Jose, both of Calif.

[73] Assignee: Inctye Pharmaceuticals, Inc., Palo Alto, Calif.

[21] Appl. No.: 09/134,593

[22] Filed: Aug. 13, 1998

Related U.S. Application Data

[62] Division of application No. 08/741,437, Oct. 31, 1996, Pat. No. 5,843,665.

[51] Int. Cl.$^6$ .............................. C12P 21/04; C12N 9/14; C12N 1/20; C07H 21/04
[52] U.S. Cl. ..................... 435/69.7; 435/195; 435/252.3; 536/23.2
[58] Field of Search .................................. 435/195, 69.7, 435/252.3; 536/23.2

[56] References Cited

PUBLICATIONS

Yang, Z., et al., "Inorganic Pyrophosphatase from Bovine Retinal Rod Outer Segments" *J. Biol. Chem.*, 267:24634–40 (1992).

Yang, Z., et al., "Molecular Cloning and Functional Expression of cDNA Encoding a Mammalian Inorganic Pyrophosphatase" *J. Biol. Chem.*, 267: 24641–47 (1992).

Lacroix, J., et al., (GI 727225), GenBank Sequence Database (Accession 727225), National Center for Biotechnology Information, National Library of Medicine, Bethesda, Maryland 20894.

Kolakowski, L.F., et al., "Cloning, molecular characterization and chromosome localization of the inorganic pyrophosphatase (PPa) gene from *S. cerevisiae*" *Nuc. Acids Re.*, 16: 10441–52 (1988).

*Primary Examiner*—Ponnathapu Achutamurthy
*Assistant Examiner*—Elizabeth Slobodyansky
*Attorney, Agent, or Firm*—Incyte Pharmaceuticals, Inc.

[57] ABSTRACT

The present invention provides a human pyrophosphatase (HPYP) and polynucleotides which identify and encode HPYP. The invention also provides genetically engineered expression vectors and host cells comprising the nucleic acid sequences encoding HPYP and a method for producing HPYP. The invention also provides for use of HPYP and agonists, antibodies, or antagonists specifically binding HPYP, in the prevention and treatment of cancer and inflammatory diseases. Additionally, the invention provides for the use of antisense molecules to polynucleotides encoding HPYP for the treatment of diseases associated with the expression of HPYP. The invention also provides diagnostic assays which utilize the polynucleotide, or fragments or the complement thereof, and antibodies specifically binding HPYP.

5 Claims, 9 Drawing Sheets

```
                        9              18          27          36          45          54
5' NNC  AAG  AGG  TTN  GGG  GCT  CTC  TCC  TTG  TCA  GTC  GGC  GCC  GCG  TGC  GGG  CTG  GTG 63             72          81          90          99         108
   GCT  CTG  TGG  CAG  CGG  CGG  CAG  CGG  CCC  TTC  TCC  GGC  ACT  ATG  AGC  TTC  AGC  ACC
                                                                      M    S    F    S    T 117            126         135         144         153         162
   GAG  GAG  CGC  GCC  GCG  CCC  TTC  TCC  CTG  GAG  TAC  CGA  GTC  TTC  CTC  AAA  AAT  GAG
    E    E    R    A    A    P    F    S    L    E    Y    R    V    F    L    K    N    E 171            180         189         198         207         216
   AAA  GGA  CAA  TAT  ATA  TCT  CCA  TTT  CAT  GAT  ATT  CCA  ATT  TAT  GCA  GAT  AAG  GAT
    K    G    Q    Y    I    S    P    F    H    D    I    P    I    Y    A    D    K    D 225            234         243         252         261         270
   GTG  TTT  CAC  ATG  GTA  GTT  GAA  GTA  CCA  CGC  TGG  TCT  AAT  GCA  AAA  ATG  GAG  ATT
    V    F    H    M    V    V    E    V    P    R    W    S    N    A    K    M    E    I 279            288         297         306         315         324
   GCT  ACA  AAG  GAC  CCT  TTA  AAC  CCT  ATT  AAA  CAA  GAT  GTG  AAA  AAA  GGA  AAA  CTT
    A    T    K    D    P    L    N    P    I    K    Q    D    V    K    K    G    K    L 333            342         351         360         369         378
   CGC  TAT  GTT  GCG  AAT  TTG  TTC  CCG  TAT  AAA  GGA  TAT  ATC  TGG  AAC  TAT  GGT  GCC
    R    Y    V    A    N    L    F    P    Y    K    G    Y    I    W    N    Y    G    A
```

FIGURE 1A

```
         387             396         405             414             423         432
ATC CCT CAG ACT TGG GAA GAC CCA GGG CAC AAT GAT AAA CAT ACT GGC TGT TGT
 I   P   Q   T   W   E   D   P   G   H   N   D   K   H   T   G   C   C 441             450         459             468             477         486
GGT GAC AAT GAC CCA ATT GAT GTG TGT GAA ATT GGA AGC AAG GTA TGT GCA AGA
 G   D   N   D   P   I   D   V   C   E   I   G   S   K   V   C   A   R 495             504         513             522             531         540
GGT GAA ATA ATT GGC GTG AAA GTT CTA GGC ATA TTG GCT ATG ATT GAC GAA GGG
 G   E   I   I   G   V   K   V   L   G   I   L   A   M   I   D   E   G 549             558         567             576             585         594
GAA ACC GAC TGG AAA GTC ATT GCC ATT AAT GTG GAT GAT CCT GAT GCA GCC AAT
 E   T   D   W   K   V   I   A   I   N   V   D   D   P   D   A   A   N 603             612         621             630             639         648
TAT AAT GAT ATC AAT GAT GTC AAA CGG CTG AAA CCT GGC TAC TTA GAA GCT ACT
 Y   N   D   I   N   D   V   K   R   L   K   P   G   Y   L   E   A   T 657             666         675             684             693         702
GTG GAC TGG TTT AGA AGG TAT AAG GTT CCT GAT GGA AAA CCA GAA AAT GAG TTT
 V   D   W   F   R   R   Y   K   V   P   D   G   K   P   E   N   E   F 711             720         729             738             747         756
GCG TTT AAT GCA GAA TTT AAA GAT AAG GAC TTT GCC ATT GAT ATT ATT AAA AGC
 A   F   N   A   E   F   K   D   K   D   F   A   I   D   I   I   K   S
```

FIGURE 1B

```
       765         774         783         792         801         810
ACT CAT GAC CAT TGG AAA GCA TTA GTG ACT AAG AAA ACG AAT GGA AAA GGA ATC
 T   H   D   H   W   K   A   L   V   T   K   K   T   N   G   K   G   I 819         828         837         846         855         864
AGT TGC ATG AAT ACA ACT TTG TCT GAG AGC CCC TTC AAG TGT GAT CCT GAT GCT
 S   C   M   N   T   T   L   S   E   S   P   F   K   C   D   P   D   A 873         882         891         900         909         918
GCC AGA GCC ATT GTG GAT GCT TTA CCA CCA CCC TGT GAA TCT GCC TGC ACA GTA
 A   R   A   I   V   D   A   L   P   P   P   C   E   S   A   C   T   V 927         936         945         954         963         972
CCA ACA GAC GTG GAT AAG TGG TTC CAT CAC CAG AAA AAC TAA TGA GAT TTC TCT
 P   T   D   V   D   K   W   F   H   H   Q   K   N   *

981         990         999        1008        1017        1026
GGA ATA CAA GCT GAT ATT GCT ACA TCG TGT TCA TCT GGA TGT ATT AGA AGT AAA 1035        1044        1053        1062        1071        1080
AGT AGT AGC TTT TCA AAG CTT TAA ATT TGT AGA ACT CAT CTA ACT AAA GTA AAT
```

FIGURE 1C

```
         1089            1098           1107          1116          1125           1134
TCT GCT GTG ACT AAT CCA ATA TAC TCA GAA TGT TAT CCA TCT AAA GCA TTT TTC 1143           1152          1161          1170          1179          1188
ATA TCT CAA CTA AGA TAA CTT TTA GCA CAT GCT TAA ATA TCA AAG CAG TTG TCA 1197           1206          1215          1224          1233          1242
TTT GGA AGT CAC TTG TGA ATA GAT GTG CAA GGG GAG CAC ATA TTG GAT GTA TAT 1251           1260          1269
GTT ACC ATA TGT TAG GAA ATA AAA TTA TTT TGC TG 3'
```

FIGURE 1D

```
  1 [M S G F S T E E R A A P F S L E Y R V F L K N E K G Q Y I S P F H D I P I Y A D]    HPYP
  1 [- - - - - - - - - - - - - - - - - - - - - - - - - - - - - - - - - - - - - - -]    g727225
  1 [M S F S S E E R A A P F T L E Y R V F L K N E K G Q Y I S P F H D I P I Y A D]      g585322
  1 [M T - Y T T R Q I G A K N T L E Y K V V Y I E K D - G K P V S A F H D I P L Y A D]  g4199

41 [K D - - V F H M V V E V P R W S N A K M E I A T K D P L N P I K Q D V K K G K L]    HPYP
  1 [- - - - - - - - - - - - - - - - - - - - - - - - - - - - - - - - - - - - - - -]    g727225
 41 [K E - - V F H M V V E V P R W S N A K M E I A T K D P L N P I K Q D V K K G K L]    g585322
 39 [K E N N I F N M V V E I P R W T N A K L E I T K E E T L N P I I Q D T K K G K L]    g4199

79 [R Y V A N L F P Y K G Y I W N Y G A I P Q T W E D P G H N D K H T G C C G D N D]    HPYP
  1 [- - N I F P Y K G Y I W N Y G T L P Q T W E D P H E K D K S T N C F G D N D]        g727225
 79 [R Y V A N L F P Y K G Y I W N Y G A I P Q T W E D P G H N D K H T G C C G D N D]    g585322
 79 [R F V R N C F P H H G Y I H N Y G A F P Q T W E D P N V S H P E T K A V G D N D]    g4199

119 [P I D V C E I G S K V C A R G E I I G V K V L G I L A M I D E G E T D W K V I A]    HPYP
 37 [P I D V C E I G S K I L S C G E V I H V K I L G I L A L I D E G E T D W K L I A]    g727225
119 [P I D V C E I G S K V C A R G E I I R V K V L G I L A M I D E G E T D W K V I A]    g585322
119 [P I D V L E I G E T I A Y T G Q V K Q V K A L G I M A L L D E G E T D W K V I A]    g4199
```

FIGURE 2A

```
159 I N V D D P D A A N Y N D I N D V K R L K P G Y L E A T V D W F R R Y K V P D G   HPYP
 77 I N A N D P E A S K F H D I D D V K K F H D I D D V K K F K P G Y L E A T L N W F R L Y K V P     g727225
159 I N V E D P D A A N Y N D I N D V K R L K P G Y L E A T V D W F R R Y K V P D G   g585322
159 I D I N D P L A P K L N D I E D V E K Y F P G L L R A T N E W F R I Y K I P D G   g4199

199 K P E N E F A F N A E F K D K D F A I D I K S T H D H W K A L V T - K K T N G     HPYP
114 K P E N E F A F N A E F K D K N F A I D I I E S T H D Y W R A L V T - K K T D G   g727225
199 K P E N Q F A F S G E A K N K K Y A L D I I K E T H D S W K Q L I A G K S S D S   g585322
199 K P E N Q F A F S G E A K N K K Y A L D I I K E T H D S W K Q L I A G K S S D S   g4199

238 K G I S C M N T T L S E S P F K C D P D A A R A I V D A L P P C - E S A C T V     HPYP
114 K G I S C M N T T V S E S P F Q C D P D A A K A I V D A L P P C - E S A C T I     g727225
238 K G I S C M N T T V S E S P F Q C D P D A A K A I V D A L P P C - E S A C T I     g585322
239 K G I D L T N V T L P D T P - - - - T Y S K A A S D A I P P A S L K A D A P I     g4199

277 P T D V D K W F H H Q K N     HPYP
114 P T D V D K W F H H Q K N     g727225
277 P T D V D K W F H H Q K N     g585322
274 D K S I D K W F F I S G S V   g4199
```

FIGURE 2B

| Library | Lib Description | Abun | Pct Abun |
|---|---|---|---|
| AMLBNOT01 | AML blast cells, blast crisis, 58 F | 1 | 0.1049 |
| THYRNOT01 | thyroid, 64 F | 3 | 0.0683 |
| TBLYNOT01 | T-B lymphoblast cell line, leukemia | 2 | 0.0651 |
| COLNTUT03 | colon tumor, 62 M, match to COLNNOT16 | 2 | 0.0543 |
| U937NOT01 | U937 monocyte cell line, 37 M | 1 | 0.0495 |
| TESTNOT01 | testis, 37 M | 1 | 0.0469 |
| HNT2AGT01 | hNT-2 cell line, post-mitotic neurons | 2 | 0.0380 |
| PROSTUT03 | prostate tumor, 67 M, match to PROSNOT05 | 1 | 0.0351 |
| LVENNOT03 | heart, left ventricle, 31 M | 1 | 0.0336 |
| BRSTNOT03 | breast, 54 F, match to BRSTTUT02 | 1 | 0.0293 |
| PANCNOT02 | pancreas, fetal M | 2 | 0.0286 |
| BEPINOM01 | bronchial epithelium, primary cell line, 54 M, NORM | 1 | 0.0273 |
| PANCTUT01 | pancreatic tumor, 65 F, match to PANCNOT08 | 1 | 0.0257 |
| MENITUT03 | brain tumor, benign meningioma, 35 F | 1 | 0.0249 |
| TMLR1DT01 | lymphocytes (non-adher PBMNC), M, 96-hr MLR | 1 | 0.0228 |
| COLNTUT02 | colon tumor, 75 M, match to COLNNOT01 | 1 | 0.0220 |
| SYNORAB01 | synovium, hip, rheumatoid, 68 F | 1 | 0.0194 |
| LUNGNOT04 | lung, 2 M | 1 | 0.0182 |
| SYNORAT04 | synovium, wrist, rheumatoid, 62 F | 1 | 0.0173 |
| NGANNOT01 | ganglioneuroma, 9 M | 1 | 0.0155 |
| BRSTNOT05 | breast, 58 F, match to BRSTTUT03 | 1 | 0.0154 |

FIGURE 5

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 289 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (A) LIBRARY:
      (B) CLONE: Consensus (xi) SEQUENCE DESCRIPTION: SEQ ID NO:1:

```
Met Ser Gly Phe Ser Thr Glu Glu Arg Ala Ala Pro Phe Ser Leu Glu
 1               5                  10                  15

Tyr Arg Val Phe Leu Lys Asn Glu Lys Gly Gln Tyr Ile Ser Pro Phe
            20                  25                  30

His Asp Ile Pro Ile Tyr Ala Asp Lys Asp Val Phe His Met Val Val
        35                  40                  45

Glu Val Pro Arg Trp Ser Asn Ala Lys Met Glu Ile Ala Thr Lys Asp
    50                  55                  60

Pro Leu Asn Pro Ile Lys Gln Asp Val Lys Lys Gly Lys Leu Arg Tyr
65                  70                  75                  80

Val Ala Asn Leu Phe Pro Tyr Lys Gly Tyr Ile Trp Asn Tyr Gly Ala
            85                  90                  95

Ile Pro Gln Thr Trp Glu Asp Pro Gly His Asn Asp Lys His Thr Gly
            100                 105                 110

Cys Cys Gly Asp Asn Asp Pro Ile Asp Val Cys Glu Ile Gly Ser Lys
            115                 120                 125

Val Cys Ala Arg Gly Glu Ile Ile Gly Val Lys Val Leu Gly Ile Leu
    130                 135                 140

Ala Met Ile Asp Glu Gly Glu Thr Asp Trp Lys Val Ile Ala Ile Asn
145                 150                 155                 160

Val Asp Asp Pro Asp Ala Ala Asn Tyr Asn Asp Ile Asn Asp Val Lys
            165                 170                 175

Arg Leu Lys Pro Gly Tyr Leu Glu Ala Thr Val Asp Trp Phe Arg Arg
            180                 185                 190

Tyr Lys Val Pro Asp Gly Lys Pro Glu Asn Glu Phe Ala Phe Asn Ala
            195                 200                 205

Glu Phe Lys Asp Lys Asp Phe Ala Ile Asp Ile Ile Lys Ser Thr His
        210                 215                 220

Asp His Trp Lys Ala Leu Val Thr Lys Lys Thr Asn Gly Lys Gly Ile
225                 230                 235                 240

Ser Cys Met Asn Thr Thr Leu Ser Glu Ser Pro Phe Lys Cys Asp Pro
            245                 250                 255

Asp Ala Ala Arg Ala Ile Val Asp Ala Leu Pro Pro Pro Cys Glu Ser
            260                 265                 270
```

Ala Cys Thr Val Pro Thr Asp Val Asp Lys Trp Phe His His Gln Lys
        275                 280                 285

Asn (2) INFORMATION FOR SEQ ID NO:2:

(i) SEQUENCE CHARACTERISTICS:
        (A) LENGTH: 1275 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:2:

CAAGAGGTTN GGGGCTCTCT CCTTGTCAGT CGGCGCCGCG TGCGGGCTGG TGGCTCTGTG    60

GCAGCGGCGG CGGCAGGACT CCGGCACTAT GAGCGGCTTC AGCACCGAGG AGCGCGCCGC   120

GCCCTTCTCC CTGGAGTACC GAGTCTTCCT CAAAAATGAG AAAGGACAAT ATATATCTCC   180

ATTTCATGAT ATTCCAATTT ATGCAGATAA GGATGTGTTT CACATGGTAG TTGAAGTACC   240

ACGCTGGTCT AATGCAAAAA TGGAGATTGC TACAAAGGAC CCTTTAAACC CTATTAAACA   300

AGATGTGAAA AAGGAAAAC TTCGCTATGT TGCGAATTTG TTCCCGTATA AAGGATATAT   360

CTGGAACTAT GGTGCCATCC CTCAGACTTG GAAGACCCA GGGCACAATG ATAAACATAC   420

TGGCTGTTGT GGTGACAATG ACCCAATTGA TGTGTGTGAA ATTGGAAGCA AGGTATGTGC   480

AAGAGGTGAA ATAATTGGCG TGAAAGTTCT AGGCATATTG GCTATGATTG ACGAAGGGGA   540

AACCGACTGG AAAGTCATTG CCATTAATGT GGATGATCCT GATGCAGCCA ATTATAATGA   600

TATCAATGAT GTCAAACGGC TGAAACCTGG CTACTTAGAA GCTACTGTGG ACTGGTTTAG   660

AAGGTATAAG GTTCCTGATG GAAAACCAGA AAATGAGTTT GCGTTTAATG CAGAATTTAA   720

AGATAAGGAC TTTGCCATTG ATATTATTAA AAGCACTCAT GACCATTGGA AAGCATTAGT   780

GACTAAGAAA ACGAATGGAA AAGGAATCAG TTGCATGAAT ACAACTTTGT CTGAGAGCCC   840

CTTCAAGTGT GATCCTGATG CTGCCAGAGC CATTGTGGAT GCTTTACCAC CACCCTGTGA   900

ATCTGCCTGC ACAGTACCAA CAGACGTGGA TAAGTGGTTC CATCACCAGA AAAACTAATG   960

AGATTTCTCT GGAATACAAG CTGATATTGC TACATCGTGT TCATCTGGAT GTATTAGAAG  1020

TAAAAGTAGT AGCTTTTCAA AGCTTTAAAT TTGTAGAACT CATCTAACTA AAGTAAATTC  1080

TGCTGTGACT AATCCAATAT ACTCAGAATG TTATCCATCT AAAGCATTTT TCATATCTCA  1140

ACTAAGATAA CTTTTAGCAC ATGCTTAAAT ATCAAAGCAG TTGTCATTTG GAAGTCACTT  1200

GTGAATAGAT GTGCAAGGGG AGCACATATT GGATGTATAT GTTACCATAT GTTAGGAAAT  1260

AAAATTATTT TGCTG                                                   1275

(2) INFORMATION FOR SEQ ID NO:3:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank (B) CLONE: 727225

(xi) SEQUENCE DESCRIPTION: SEQ ID NO:3:

Asn Ile Phe Pro Tyr Lys Gly Tyr Ile Trp Asn Tyr Gly Thr Leu Pro
 1               5                  10                  15

Gln Thr Trp Glu Asp Pro His Glu Lys Asp Lys Ser Thr Asn Cys Phe
             20                  25                  30

Gly Asp Asn Asp Pro Ile Asp Val Cys Glu Ile Gly Ser Lys Ile Leu
         35                  40                  45

Ser Cys Gly Glu Val Ile His Val Lys Ile Leu Gly Ile Leu Ala Leu
 50                  55                  60

Ile Asp Glu Gly Glu Thr Asp Trp Lys Leu Ile Ala Ile Asn Ala Asn
65                  70                  75                  80

Asp Pro Glu Ala Ser Lys Phe His Asp Ile Asp Asp Val Lys Lys Phe
                85                  90                  95

Lys Pro Gly Tyr Leu Glu Ala Thr Leu Asn Trp Phe Arg Leu Tyr Lys
             100                 105                 110

Val Pro (2) INFORMATION FOR SEQ ID NO:4:

(i) SEQUENCE CHARACTERISTICS:
        (A) LENGTH: 289 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 585322

(xi) SEQUENCE DESCRIPTION: SEQ ID NO:4:

Met Ser Ser Phe Ser Ser Glu Glu Arg Ala Ala Pro Phe Thr Leu Glu
 1               5                  10                  15

Tyr Arg Val Phe Leu Lys Asn Gly Lys Gly Gln Tyr Ile Ser Pro Phe
             20                  25                  30

His Asp Ile Pro Ile Tyr Ala Asp Lys Glu Val Phe His Met Val Val
         35                  40                  45

Glu Val Pro Arg Trp Ser Asn Ala Lys Met Glu Ile Ala Thr Lys Asp
 50                  55                  60

Pro Leu Asn Pro Ile Lys Gln Asp Val Lys Lys Gly Lys Leu Arg Tyr
65                  70                  75                  80

Val Ala Asn Leu Phe Pro Tyr Lys Gly Tyr Ile Trp Asn Tyr Gly Ala
                85                  90                  95

Ile Pro Gln Thr Trp Glu Asp Pro Gly His Asn Asp Lys His Thr Gly
             100                 105                 110

Cys Cys Gly Asp Asn Asp Pro Ile Asp Val Cys Glu Ile Gly Ser Lys
         115                 120                 125

Val Cys Ala Arg Gly Glu Ile Ile Arg Val Lys Val Leu Gly Ile Leu
         130                 135                 140

Ala Met Ile Asp Glu Gly Glu Thr Asp Trp Lys Val Ile Ala Ile Asn
145                 150                 155                 160

Val Glu Asp Pro Asp Ala Ala Asn Tyr Asn Asp Ile Asn Asp Val Lys
                165                 170                 175

Arg Leu Lys Pro Gly Tyr Leu Glu Ala Thr Val Asp Trp Phe Arg Arg
             180                 185                 190

```
Tyr Lys Val Pro Asp Gly Lys Pro Glu Asn Glu Phe Ala Phe Asn Ala
        195                 200                 205

Glu Phe Lys Asp Lys Asn Phe Ala Ile Asp Ile Ile Glu Ser Thr His
        210                 215                 220

Asp Tyr Trp Arg Ala Leu Val Thr Lys Thr Asp Gly Lys Gly Ile
225                 230                 235                 240

Ser Cys Met Asn Thr Thr Val Ser Glu Ser Pro Phe Gln Cys Asp Pro
                    245                 250                 255

Asp Ala Ala Lys Ala Ile Val Asp Ala Leu Pro Pro Cys Glu Ser
                260                 265                 270

Ala Cys Thr Ile Pro Thr Asp Val Asp Lys Trp Phe His His Gln Lys
                275                 280                 285

Asn
```

(2) INFORMATION FOR SEQ ID NO:5:

(i) SEQUENCE CHARACTERISTICS:
        (A) LENGTH: 287 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 4199

(xi) SEQUENCE DESCRIPTION: SEQ ID NO:5:

```
Met Thr Tyr Thr Thr Arg Gln Ile Gly Ala Lys Asn Thr Leu Glu Tyr
1               5                   10                  15

Lys Val Tyr Ile Glu Lys Asp Gly Lys Pro Val Ser Ala Phe His Asp
            20                  25                  30

Ile Pro Leu Tyr Ala Asp Lys Glu Asn Asn Ile Phe Asn Met Val Val
            35                  40                  45

Glu Ile Pro Arg Trp Thr Asn Ala Lys Leu Glu Ile Thr Lys Glu Glu
    50                  55                  60

Thr Leu Asn Pro Ile Ile Gln Asp Thr Lys Lys Gly Lys Leu Arg Phe
65                  70                  75                  80

Val Arg Asn Cys Phe Pro His His Gly Tyr Ile His Asn Tyr Gly Ala
                85                  90                  95

Phe Pro Gln Thr Trp Glu Asp Pro Asn Val Ser His Pro Glu Thr Lys
                100                 105                 110

Ala Val Gly Asp Asn Asp Pro Ile Asp Val Leu Glu Ile Gly Glu Thr
            115                 120                 125

Ile Ala Tyr Thr Gly Gln Val Lys Gln Val Lys Ala Leu Gly Ile Met
        130                 135                 140

Ala Leu Leu Asp Glu Gly Glu Thr Asp Trp Lys Val Ile Ala Ile Asp
145                 150                 155                 160

Ile Asn Asp Pro Leu Ala Pro Lys Leu Asn Asp Ile Glu Asp Val Glu
                165                 170                 175

Lys Tyr Phe Pro Gly Leu Leu Arg Ala Thr Asn Glu Trp Phe Arg Ile
            180                 185                 190

Tyr Lys Ile Pro Asp Gly Lys Pro Glu Asn Gln Phe Ala Phe Ser Gly
        195                 200                 205

Glu Ala Lys Asn Lys Lys Tyr Ala Leu Asp Ile Ile Lys Glu Thr His
        210                 215                 220

Asp Ser Trp Lys Gln Leu Ile Ala Gly Lys Ser Ser Asp Ser Lys Gly
```

-continued

```
225                 230                 235                 240

Ile Asp Leu Thr Asn Val Thr Leu Pro Asp Thr Pro Thr Tyr Ser Lys
                245                 250                 255

Ala Ala Ser Asp Ala Ile Pro Pro Ala Ser Leu Lys Ala Asp Ala Pro
                260                 265                 270

Ile Asp Lys Ser Ile Asp Lys Trp Phe Phe Ile Ser Gly Ser Val
            275                 280                 285
```

HUMAN PYROPHOSPHATASE

This application is a divisional application of U.S. application Ser. No. 08/741,437, filed Oct. 31, 1996 now U.S. Pat. No. 5,843,665.

FIELD OF THE INVENTION

This invention relates to nucleic acid and amino acid sequences of a novel inorganic pyrophosphatase and to the use of these sequences in the diagnosis, prevention, and treatment of inflammatory diseases and cancer.

BACKGROUND OF THE INVENTION

Inorganic pyrophosphate (PPi) is produced in living cells in numerous metabolic pathways. These include the synthesis of polymers such as DNA, RNA, protein, and polysaccharides as well as small molecules such as cyclic-GMP and cyclic-AMP. PPi is also produced by oxidative phosphorylation and glycolysis. Most of these reactions are readily reversible in the presence of excess PPi, and PPi, itself, inhibits some of the cellular enzymes involved in these metabolic pathways. In order to promote the forward reactions and stabilize the reaction products, it is essential that PPi be removed. The enzyme pyrophosphatase (PPase) makes this energetically favorable hydrolysis of PPi possible.

PPase has been studied extensively in yeast and bacteria. Its activity has been shown to be essential for cell viability, and it may be essential for the fidelity of DNA replication as well. PPase is widely distributed in mammalian tissues where its activity varies widely. Little is known about how PPase activity is regulated in mammals or about the functions of PPase isolated from specific tissues. Multiple isoforms of PPase have, however, been found in humans and a number of other animals, perhaps indicating that there are functionally distinct isoforms of the enzyme in mammals. Bovine retina contains the highest level of PPase activity found in any mammalian tissue, and this enzyme has been sequenced and characterized (Yang, Z and Wensel, T G (1992) J Biol Chem 267: 24634–40, 24641–7). PPase activity was found to be essential for controlling PPi levels and the synthesis and degradation of cGMP which, in turn, controls the process of phototransduction in these cells.

The discovery of polynucleotides encoding pyrophosphatase, and the molecules themselves, presents the opportunity to investigate the role of pyrophosphatase in controlling the various metabolic pathways in cells involving PPi synthesis. The discovery of new pyrophosphatase molecules satisfies a need in the art by providing new diagnostic or therapeutic compositions useful in the treatment of diseases and conditions associated with uncontrolled cell signaling and cell proliferation such as inflammatory diseases and cancer.

SUMMARY OF THE INVENTION

The present invention features a novel human inorganic pyrophosphatase hereinafter designated HPYP and characterized as having similarity to pyrophosphatases from human and other sources.

Accordingly, the invention features a substantially purified HPYP having chemical homology to human, bovine, and yeast pyrophosphatases above and the amino acid sequence, SEQ ID NO:1.

One aspect of the invention features isolated and substantially purified polynucleotides that encode HPYP. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode HPYP. The present invention also features antibodies which bind specifically to HPYP, and pharmaceutical compositions comprising substantially purified HPYP. The invention also features the use of agonists and antagonists of HPYP.

BRIEF DESCRIPTION OF THE FIGURES

FIGS. 1A, 1B, 1C and 1D show the amino acid sequence (SEQ ID NO: 1) and nucleic acid sequence (SEQ ID NO:2) of HPYP. The alignment was produced using MACDNASIS PRO™ software (Hitachi Software Engineering Co., Ltd., San Bruno, Calif.).

FIG. 2A and 2B show the amino acid sequence alignments among HPYP (SEQ ID NO:1), a partial sequence of the human pyrophosphatase (GI 727225; SEQ ID NO:3), bovine pyrophosphatase (GI 585322; SEQ ID NO:4) and yeast pyrophosphatase (GI 4199; SEQ ID NO:5). The alignment was produced using the multisequence alignment program of DNASTAR™ software (DNASTAR Inc, Madison Wis.).

FIG. 5 shows the northern analysis for SEQ ID NO:2. The northern analysis was produced electronically using LIFESEQ FL® database (Incyte Pharmaceuticals, Inc., Palo Alto, Calif.).

DESCRIPTION OF THE INVENTION

Figure 3:
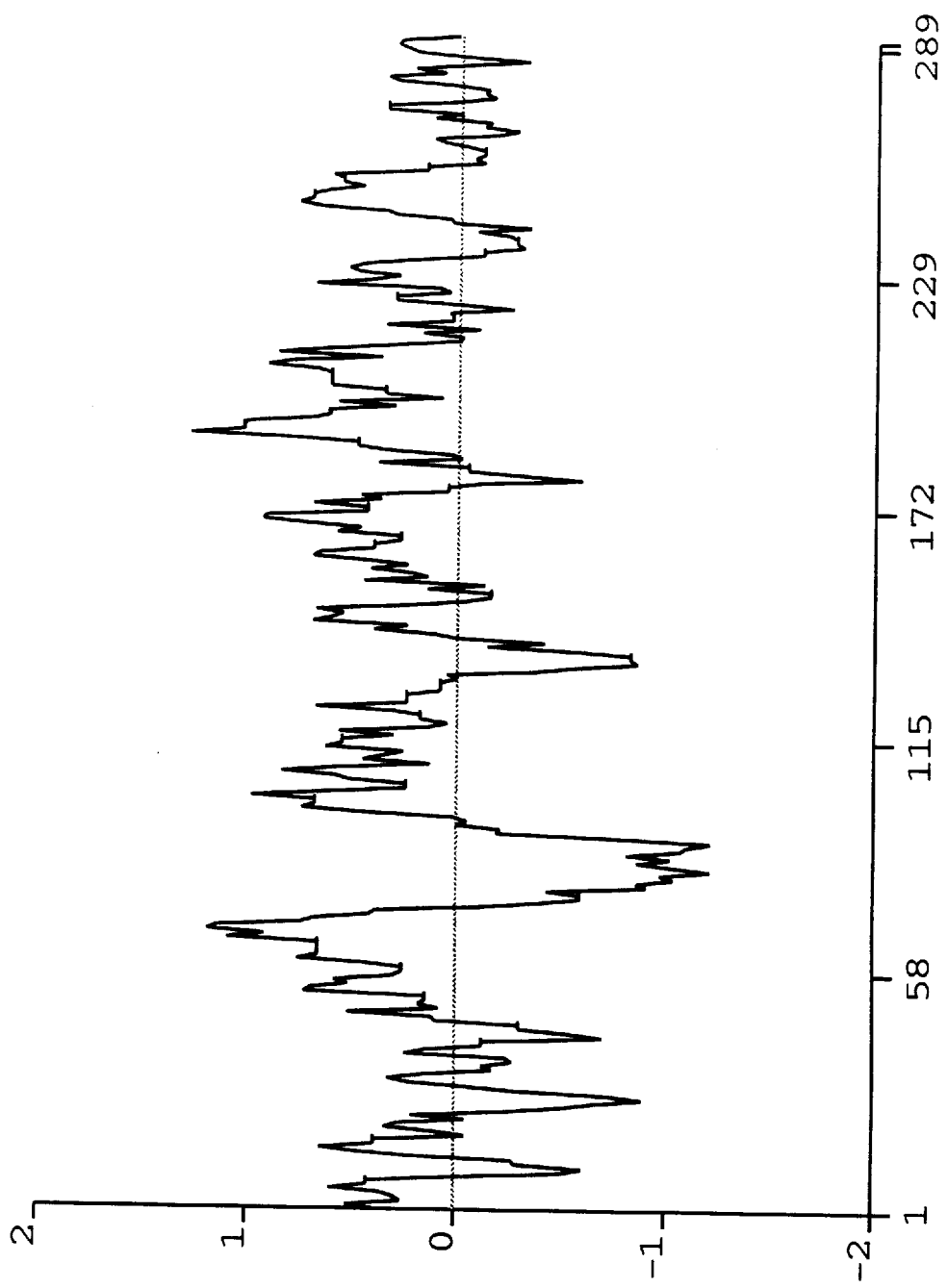
FIG. 3 shows the hydrophobicity plot (MACDNASIS PRO™) for HPYP, SEQ ID NO:1; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8: 53–63).

HPYP, as used herein, refers to the amino acid sequences of substantially purified HPYP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of HPYP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HPYP, or any oligopeptide thereof, to induce a specific immune response in appropriate animals or cells and to bind with specific antibodies.

The term "agonist", as used herein, refers to a molecule which, when bound to HPYP, causes a change in HPYP which modulates the activity of HPYP. Agonists may include proteins, nucleic acids, carbohydrates, or any other molecules which bind to HPYP.

The terms "antagonist" or "inhibitor", as used herein, refer to a molecule which, when bound to HPYP, blocks the biological or immunological activity of HPYP. Antagonists and inhibitors may include proteins, nucleic acids, carbohydrates, or any other molecules which bind to HPYP.

The term "modulate", as used herein, refers to a change or an alteration in the biological activity of HPYP. Modulation may be an increase or a decrease in protein activity, a change in binding characteristics, or any other change in the biological, functional or immunological properties of HPYP.

The term "mimetic", as used herein, refers to a molecule, the structure of which is developed from knowledge of the structure of HPYP or portions thereof and, as such, is able to effect some or all of the actions of [REF PROT]-like molecules.

The term "derivative", as used herein, refers to the chemical modification of a nucleic acid encoding HPYP or the encoded HPYP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human HPYP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HPYP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding HPYP in a sample and thereby correlates with expression of the transcript from the polynucleotide encoding the protein.

"Alterations" in the polynucleotide of SEQ ID NO:2, as used herein, comprise any alteration in the sequence of polynucleotides encoding HPYP including deletions, insertions, and point mutations that may be detected using hybridization assays. Included within this definition is the detection of alterations to the genomic DNA sequence which encodes HPYP (e.g., by alterations in the pattern of restriction fragment length polymorphisms capable of hybridizing to SEQ ID NO:2), the inability of a selected fragment of SEQ ID NO: 2 to hybridize to a sample of genomic DNA (e.g., using allele-specific oligonucleotide probes), and improper or unexpected hybridization, such as hybridization to a locus other than the normal chromosomal locus for the polynucleotide sequence encoding HPYP (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind HPYP polypeptides can be prepared using intact polypeptides or fragments containing small peptides of interest as the immunizing antigen. The polypeptide or peptide used to immunize an animal can be derived from translated RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of a novel human pyrophosphatase (HPYP), the polynucleotides encoding HPYP, and the use of these compositions for the diagnosis, prevention, or treatment of inflammatory diseases and cancer.

Nucleic acids encoding the human HPYP of the present invention were first identified in Incyte Clone 768320 from the lung tissue cDNA library LUNGNOT04 through a computer-generated search for amino acid sequence alignments. A consensus sequence, SEQ ID NO:2, was derived from the following overlapping and/or extended nucleic acid sequences: Incyte Clones 000769 and 002394/U937NOT01, 768320/LUNGNOT04, 853164/NGANNOT01, and 1283643/COLNNOT16.

Figure 4:
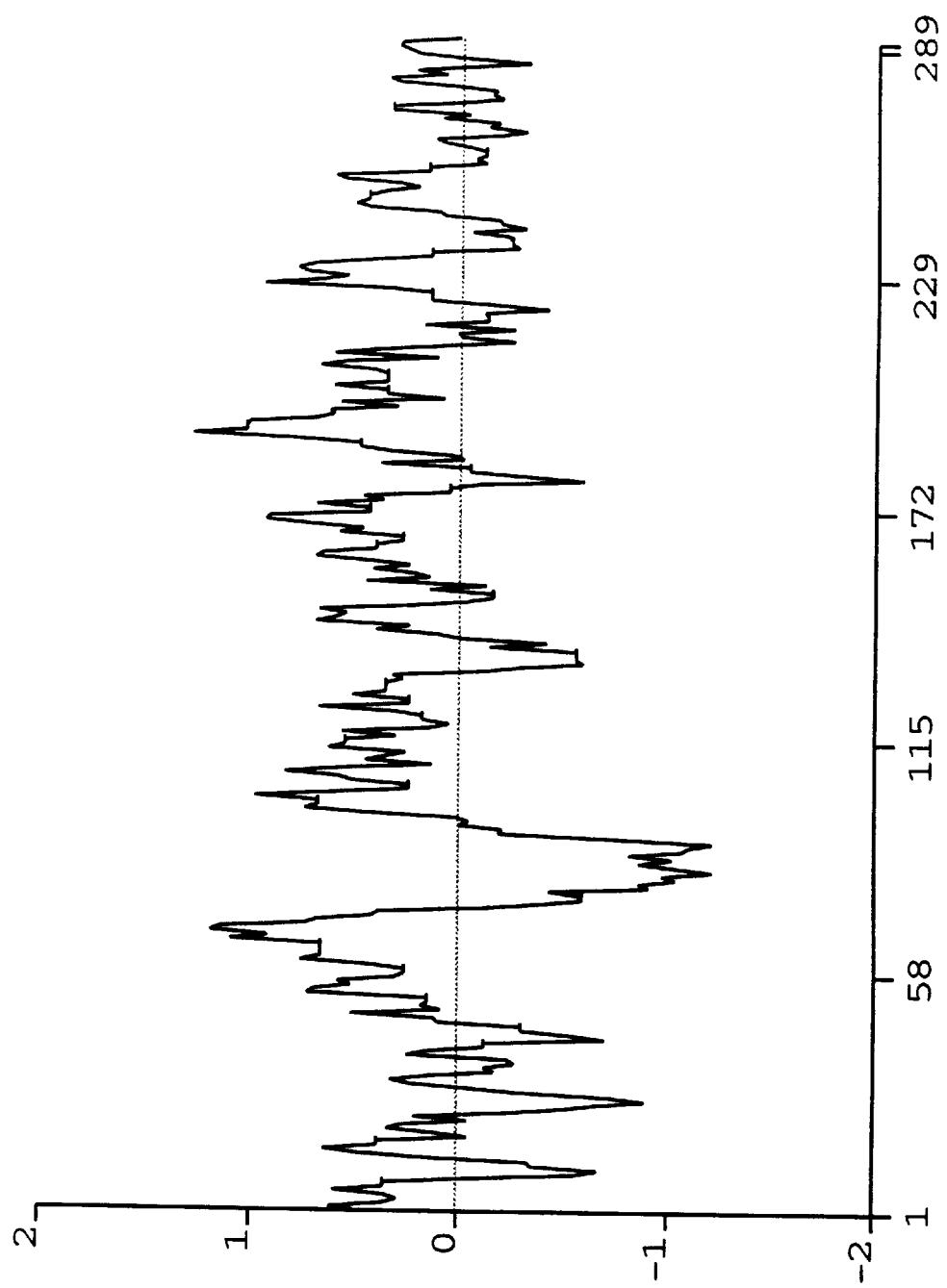
FIG. 4 shows the hydrophobicity plot for bovine pyrophosphatase, SEQ ID NO:4.

In one embodiment, the invention encompasses the novel human pyrophosphatase, a polypeptide comprising the amino acid sequence of SEQ ID NO:1, as shown in FIGS. 1A, 1B, 1C and 1D. HPYP is 289 amino acids in length and has chemical and structural homology with the partial sequence of a human pyrophosphatase (GI 727225; SEQ ID NO:3), a bovine pyrophosphatase (GI 585322; SEQ ID NO:4) and a yeast pyrophosphatase (GI 4199; SEQ ID NO:5). In particular, HPYP shares 77% identity with the partial human pyrophosphatase sequence (SEQ ID NO:3) over the length of that molecule. The bovine and yeast pyrophosphatases each share 96% and 37% identity with HPYP, respectively. Despite the wide variation in overall sequence identity between these four molecules, all of them contain the seventeen amino acid residues previously identified as being important for enzyme activity in Ppase (Lahti, Ret al (1990) Biochim Biophys Acta 1038: 338–345). In particular, the sequence, DEGETDWK, beginning at D(148) is identical for all four molecules. As illustrated by FIGS. 3 and 4, HPYP and bovine pyrophosphatase have rather similar hydrophobicity plots. Northern analysis (FIG. 5) shows the expression of this sequence in various libraries, at least 43% of which are immortalized or cancerous and at least 24% of which involve immune response. Of particular note is the expression in thyroid tissue, colon tumor, and rheumatoid arthritis.

The invention also encompasses HPYP variants. A preferred HPYP variant is one having at least 80%, and more preferably 90%, amino acid sequence similarity to the HPYP amino acid sequence (SEQ ID NO:1). A most preferred HPYP variant is one having at least 95% amino acid sequence similarity to SEQ ID NO:1.

The invention also encompasses polynucleotides which encode HPYP. Accordingly, any nucleic acid sequence which encodes the amino acid sequence of HPYP can be used to generate recombinant molecules which express HPYP. In a particular embodiment, the invention encompasses the polynucleotide comprising the nucleic acid of SEQ ID NO:2 as shown in FIGS. 1A, 1B, 1C and 1D.

It will be appreciated by those skilled in the art that as a result of the degeneracy of the genetic code, a multitude of nucleotide sequences encoding HPYP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HPYP, and all such variations are to be considered as being specifically disclosed.

Although nucleotide sequences which encode HPYP and its variants are preferably capable of hybridizing to the nucleotide sequence of the naturally occurring HPYP under appropriately selected conditions of stringency, it may be advantageous to produce nucleotide sequences encoding HPYP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HPYP and its derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode HPYP and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding HPYP or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Kimmel, A. R. (1987; Methods Enzymol. Vol. 152), and may be used at a defined stringency.

Altered nucleic acid sequences encoding HPYP which are encompassed by the invention include deletions, insertions, or substitutions of different nucleotides resulting in a polynucleotide that encodes the same or a functionally equivalent HPYP. The encoded protein may also contain deletions, insertions, or substitutions of amino acid residues which produce a silent change and result in a functionally equivalent HPYP. Deliberate amino acid substitutions may be made on the basis of similarity in polarity, charge, solubility, hydrophobicity, hydrophilicity, and/or the amphipathic nature of the residues as long as the biological activity of HPYP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding HPYP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE® (U.S. Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The polynucleotide sequence encoding HPYP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2: 318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16: 8186). The primers may be designed using OLIGO® 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1: 111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19: 3055–3060). Additionally, one may use PCR, nested primers, and PROMOTERFINDER™ libraries to walk in genomic DNA (Clontech, Palo Alto, Calif.). This process avoids the need to screen libraries and may be is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HPYP, or fusion proteins or functional equivalents thereof, may be used in recombinant DNA molecules to direct expression of HPYP in appropriate host cells. Due to the inherent degeneracy of the genetic code, other DNA sequences which encode substantially the same or a functionally equivalent amino acid sequence may be produced and these sequences may be used to clone and express HPYP.

As will be understood by those of skill in the art, it may be advantageous to produce HPYP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the HPYP coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, a natural, modified, or recombinant polynucleotide encoding HPYP may be ligated to a heterologous sequence to encode a fusion protein. For example, to screen peptide libraries for inhibitors of HPYP activity, it may be useful to encode a chimeric HPYP protein that can be recognized by a commercially available antibody. A fusion protein may also be engineered to contain a cleavage site located between a HPYP encoding sequence and the heterologous protein sequence, so that HPYP may be cleaved and purified away from the heterologous moiety.

In another embodiment, the coding sequence of HPYP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the HPYP amino acid sequence, or a portion thereof. For example, peptide synthesis can be performed using various solid-phase techniques (Roberge, J. Y. et al. (1995) Science 269: 202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of HPYP, or any part thereof, may be altered during direct synthesis and/or combined using chemical methods with sequences from other proteins, or any part thereof, to produce a variant polypeptide.

In order to express a biologically active HPYP, the nucleotide sequence encoding HPYP or functional equivalents, may be inserted into an appropriate expression vector, i.e., a vector which contains the necessary elements for the transcription and translation of the inserted coding sequence.

Methods which are well known to those skilled in the art may be used to construct expression vectors containing a HPYP coding sequence and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express a HPYP coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, CALIF.) or PSPORT™ plasmid (Gibco BRL) and ptrp-lac hybrids, and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HPYP, vectors based on SV40 or EBV may be used with an appropriate selectable marker.

In bacterial systems, a number of expression vectors may be selected depending upon the use intended for HPYP. For example, when large quantities of HPYP are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding HPYP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264: 5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153: 516–544.

In cases where plant expression vectors are used, the expression of a sequence encoding HPYP may be driven by any of a number of promoters. For example, viral promoters such as the 35S and 19S promoters of CaMV may be used alone or in combination with the omega leader sequence from TMV (Takamatsu, N. (1987) EMBO J. 6: 307–311). Alternatively, plant promoters such as the small subunit of RUBISCO or heat shock promoters may be used (Coruzzi, G. et al. (1984) EMBO J. 3: 1671–1680; Broglie, R. et al. (1984) Science 224: 838–843; Winter, J. et al. (1991) Results Probl. Cell Differ. 17: 85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HPYP. For example, in one such system, *Autographa californica* nuclear polyhedrosis virus (*Ac*NPV) is used as a vector to express foreign genes in *Spodoptera frugiperda* cells or in Trichoplusia larvae. The sequence encoding HPYP may be cloned into a non-essential region of the virus, such as the polyhedrin gene, and placed under control of the polyhedrin promoter. Successful insertion of HPYP will render the polyhedrin gene inactive and produce recombinant virus lacking coat protein. The recombinant viruses may then be used to infect, for example, S. frugiperda cells or Trichoplusia larvae in which HPYP may be expressed (Engelhard, E. K. et al. (1994) Proc. Nat. Acad. Sci. 91: 3224–3227).

In mammalian host cells, a number of viral-based expression systems may be utilized. In cases where an adenovirus is used as an expression vector, a sequence encoding HPYP may be ligated into an adenovirus transcription/translation complex consisting of the late promoter and tripartite leader sequence. Insertion in a non-essential E1 or E3 region of the viral genome may be used to obtain a viable virus which is capable of expressing HPYP in infected host cells (Logan, J. and Shenk, T. (1984) Proc. Natl. Acad. Sci. 81: 3655–3659). In addition, transcription enhancers, such as the Rous sarcoma virus (RSV) enhancer, may be used to increase expression in mammalian host cells.

Specific initiation signals may also be used to achieve more efficient translation of a sequence encoding HPYP. Such signals include the ATG initiation codon and adjacent sequences. In cases where sequences encoding HPYP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20: 125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HPYP may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11: 223–32) and adenine phosphoribosyltransferase (Lowy, I. et al. (1980) Cell 22: 817–23) genes which can be employed in tk- or aprt- cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77: 3567–70); npt, which confers resistance to the aminoglycosides neomycin and G-418 (Colbere-Garapin, F. et al (1981) J. Mol. Biol. 150: 1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85: 8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55: 121–131).

Although the presence/absence of marker gene expression suggests that the gene of interest is also present, its presence and expression may need to be confirmed. For example, if the sequence encoding HPYP is inserted within a marker gene sequence, recombinant cells containing sequences encoding HPYP can be identified by the absence of marker gene function. Alternatively, a marker gene can be placed in tandem with a sequence encoding HPYP under the control of a single promoter. Expression of the marker gene in response to induction or selection usually indicates expression of the tandem gene as well.

Alternatively, host cells which contain the coding sequence for HPYP and express HPYP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of the nucleic acid or protein.

The presence of the polynucleotide sequence encoding HPYP can be detected by DNA-DNA or DNA-RNA hybridization or amplification using probes or portions or fragments of polynucleotides encoding HPYP. Nucleic acid amplification based assays involve the use of oligonucleotides or oligomers based on the HPYP-encoding sequence to detect transformants containing DNA or RNA encoding HPYP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HPYP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HPYP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983) J. Exp. Med. 158: 1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HPYP include oligolabeling, nick translation, end-labeling or PCR amplification using a labeled nucleotide. Alternatively, the sequence encoding HPYP, or any portion of it, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a nucleotide sequence encoding HPYP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HPYP may be designed to contain signal sequences which direct secretion of HPYP through a prokaryotic or eukaryotic cell membrane. Other recombinant constructions may be used to join sequences encoding HPYP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HPYP may be used to facilitate purification. One such expression vector provides for expression of a fusion protein containing HPYP and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying HPYP from the fusion protein. A discussion of vectors which contain fusion proteins is provided in Kroll, D. J. et al. (1993; DNA Cell Biol. 12: 441–453).

In addition to recombinant production, fragments of HPYP may be produced by direct peptide synthesis using solid-phase techniques (cf Stewart et al. (1969) *Solid-Phase Peptide Synthesis*, W. H. Freeman Co., San Francisco, Calif.; Merrifield J. (1963) J. Am. Chem. Soc. 85: 2149–2154). Protein synthesis may be performed using manual techniques or by automation. Automated synthesis may be achieved, for example, using Applied Biosystems 431A Peptide Synthesizer (Perkin Elmer). Various fragments of HPYP may be chemically synthesized separately and combined using chemical methods to produce the full length molecule Therapeutic Applications In another embodiment of the invention, HPYP or fragments thereof may be used for therapeutic purposes.

Since cGMP and cAMP are important elements of cell signaling pathways in virtually all cells and tissues, the control of specific PPase activity in specific cell types could provide a mechanism for controlling cell signaling and be useful in the treatment of diseases and conditions associated with uncontrolled cell signaling and cell proliferation such as inflammatory diseases and cancer.

Based on the chemical and structural homology among HPYP (SEQ ID NO:1), other pyrophosphatases and northern analysis (FIG. 5) which shows that approximately 50% of the libraries containing HPYP transcripts are associated with either cancer or immune response, expression of HPYP is believed to function in cancer, particularly cancers of the colon, prostate, brain, and pancreas, and in inflammatory disease. In addition, the known function of PPases in promoting cell metabolic reactions and cell growth suggest that HPYP may be useful in promoting cell and tissue regeneration.

Therefore, in one embodiment of the invention, HPYP, a fragment or derivative thereof, a vector expressing HPYP, a fragment or derivative thereof, may be used to trigger the regeneration of cells, tissues, or organs which were previously differentiated or not easily regenerated. This would be especially useful in, but is not limited to, the regeneration or transplantation and development of nerve, pancreatic, bone marrow, prostate tissue, and would involve supplying various natural molecules, such as HPYP, in drug regimes that allow cell division and differentiation to occur. Small amounts of new functional tissue have the capacity to greatly improve the quality of life for victims of accidents or degenerative hereditary diseases.

Since expression of HPYP is highly correlated with cancer (FIG. 5), vectors expressing antisense, and antagonists or inhibitors of the protein may be used to inhibit the expression or activity of HPYP as a means of suppressing tumor cell growth. Control of HPYP activity as a novel approach to cancer treatment may be especially useful in combination therapy with other chemotherapeutic agents. Such combinations of therapeutic agents having different cellular mechanisms of action often have synergistic effects allowing the use of lower effective doses of each agent and lessening side effects.

In another embodiment, vectors expressing antisense, and antagonists or inhibitors of the protein may be used to suppress the excessive proliferation of inflammatory cells which cause damage in immunological diseases. Such immune diseases include, but are not limited to, anemias, asthma, systemic lupus, and myasthenia gravis, diabetes mellitus, osteoporosis, glomerulonephritis; rheumatoid and osteoarthritis; and scleroderma.

In another embodiment, antagonists which block or modulate the effect of HPYP may be used in those situations where such inhibition is therapeutically desirable. Such antagonists or inhibitors may be produced using methods which are generally known in the art, and include particularly the use of purified HPYP to produce antibodies or to screen libraries of pharmaceutical agents for those which specifically bind HPYP. For example, in one aspect, antibodies which are specific for HPYP may be used directly as an antagonist, or indirectly as a targeting or delivery mechanism for bringing a pharmaceutical agent to cells or tissue which express HPYP.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HPYP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HPYP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HPYP amino acids may be fused with those of another protein such as keyhole limpet hemocyanin and antibody produced against the chimeric molecule.

Monoclonal antibodies to HPYP may be prepared using any technique which provides for the production of antibody molecules by continuous cell lines in culture. These include, but are not limited to, the hybridoma technique, the human B-cell hybridoma technique, and the EBV-hybridoma technique (Koehler et al. (1975) Nature 256: 495–497; Kosbor et al. (1983) Immunol. Today 4: 72; Cote et al. (1983) Proc. Natl. Acad. Sci. 80: 2026–2030; Cole et al. (1985) *Monoclonal Antibodies and Cancer Therapy*, Alan R. Liss Inc., New York, N.Y., pp. 77–96).

In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. 81: 6851–6855; Neuberger et al. (1984) Nature 312: 604–608; Takeda et al. (1985) Nature 314: 452–454). Alternatively, techniques described for the production of single chain antibodies may be adapted, using methods known in the art, to produce HPYP-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88: 11120–3).

Antibodies may also be produced by inducing in vivo production in the lymphocyte population or by screening recombinant immunoglobulin libraries or panels of highly specific binding reagents as disclosed in the literature (Orlandi, et al. (1989) Proc. Natl. Acad. Sci. 86: 3833–3837; Winter, G. et al. (1991) Nature 349: 293–299).

Antibody fragments which contain specific binding sites for HPYP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 256: 1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HPYP and its specific antibody. A two-site, monoclonal-based immunoassay utilizing monoclonal antibodies reactive to two non-interfering HPYP epitopes is preferred, but a competitive binding assay may also be employed (Maddox, supra).

In another embodiment of the invention, the polynucleotides encoding HPYP, or any fragment thereof, or antisense sequences, may be used for therapeutic purposes. In one aspect, antisense to the polynucleotide encoding HPYP may be used in situations in which it would be desirable to block the synthesis of the protein. In particular, cells may be transformed with sequences complementary to polynucleotides encoding HPYP. Thus, antisense sequences may be used to modulate HPYP activity, or to achieve regulation of gene function. Such technology is now well known in the art, and sense or antisense oligomers or larger fragments, can be designed from various locations along the coding or control regions of sequences encoding HPYP.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding HPYP. These techniques are described both in Sambrook et al. (supra) and in Ausubel et al. (supra).

Genes encoding HPYP can be turned off by transforming a cell or tissue with expression vectors which express high levels of a polynucleotide or fragment thereof which encodes HPYP. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HPYP, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HPYP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HPYP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HPYP, antibodies to HPYP, mimetics, agonists, antagonists, or inhibitors of HPYP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose, gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HPYP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HPYP or fragments thereof, antibodies of HPYP, agonists, antagonists or inhibitors of HPYP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HPYP may be used for the diagnosis of conditions or diseases characterized by expression of HPYP, or in assays to monitor patients being treated with HPYP, agonists, antagonists or inhibitors. The antibodies useful for diagnostic purposes may be prepared in the same manner as those described above for therapeutics. Diagnostic assays for HPYP include methods which utilize the antibody and a label to detect HPYP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HPYP are known in the art and provide a basis for diagnosing altered or abnormal levels of HPYP expression. Normal or standard values for HPYP expression are established by combining body fluids or cell extracts taken from normal mammalian subjects, preferably human, with antibody to HPYP under conditions suitable for complex formation The amount of standard complex formation may be quantified by various methods, but preferably by photometric, means. Quantities of HPYP expressed in subject, control and disease, samples from biopsied tissues are compared with the standard values. Deviation between standard and subject values establishes the parameters for diagnosing disease.

In another embodiment of the invention, the polynucleotides encoding HPYP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HPYP may be correlated with disease. The diagnostic assay may be used to distinguish between absence, presence, and excess expression of HPYP, and to monitor regulation of HPYP levels during therapeutic intervention.

In one aspect, hybridization with PCR probes which are capable of detecting polynucleotide sequences, including genomic sequences, encoding HPYP or closely related molecules, may be used to identify nucleic acid sequences which encode HPYP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HPYP, alleles, or related sequences.

Probes may also be used for the detection of related sequences, and should preferably contain at least 50% of the nucleotides from any of the HPYP encoding sequences. The hybridization probes of the subject invention may be DNA or RNA and derived from the nucleotide sequence of SEQ ID NO:2 or from genomic sequence including promoter, enhancer elements, and introns of the naturally occurring HPYP.

Means for producing specific hybridization probes for DNAs encoding HPYP include the cloning of nucleic acid sequences encoding HPYP or HPYP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HPYP may be used for the diagnosis of conditions or diseases which are associated with expression of HPYP. Examples of such conditions or diseases include cancers of the colon, prostate, brain, and pancreas and inflammatory diseases such as anemias, asthma, systemic lupus, and myasthenia gravis, diabetes mellitus, osteoporosis, glomerulonephritis; rheumatoid and osteoarthritis; and scleroderma. The polynucleotide sequences encoding HPYP may be used in Southern or northern analysis, dot blot, or other membrane-based technologies; in PCR technologies; or in dip stick, pin, ELISA or chip assays utilizing fluids or tissues from patient biopsies to detect altered HPYP expression. Such qualitative or quantitative methods are well known in the art.

In a particular aspect, the nucleotide sequences encoding HPYP may be useful in assays that detect activation or induction of various cancers, particularly those mentioned above. The nucleotide sequence encoding HPYP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequence has hybridized with nucleotide sequences in the sample, and the presence of altered levels of nucleotide sequences encoding HPYP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HPYP, a normal or standard profile for expression is established. This may be accomplished by combining body fluids or cell extracts taken from normal subjects, either animal or human, with a sequence, or a fragment thereof, which encodes HPYP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides encoding HPYP may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/ or quantitation of closely related DNA or RNA sequences.

Methods which may also be used to quantitate the expression of HPYP include radiolabeling or biotinylating nucleotides, coamplification of a control nucleic acid, and standard curves onto which the experimental results are interpolated (Melby, P. C. et al. (1993) J. Immunol. Methods, 159: 235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequence which encodes HPYP may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7: 127–134, and Trask, B. J. (1991) Trends Genet. 7: 149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265: 1981 f). Correlation between the location of the gene encoding HPYP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336: 577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HPYP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HPYP and the agent being tested, may be measured.

Another technique for drug screening which may be used provides for high throughput screening of compounds having suitable binding affinity to the protein of interest as described in published PCT application WO84/03564. In this method, as applied to HPYP large numbers of different small test compounds are synthesized on a solid substrate, such as plastic pins or some other surface. The test compounds are reacted with HPYP, or fragments thereof, and washed. Bound HPYP is then detected by methods well known in the art. Purified HPYP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HPYP specifically compete with a test compound for binding HPYP. In this manner, the antibodies can be used to detect the presence of any peptide which shares one or more antigenic determinants with HPYP.

In additional embodiments, the nucleotide sequences which encode HPYP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I LUNGNOT04 cDNA Library Construction

The LUNGNOT04 cDNA library was constructed from lung tissue obtained from a 2-year-old male (specimen #RU95-09-0664; International Institute of Advanced Medicine, Exton Pa.) who died of anoxia. The cells were lysed using a Brinkmann Homogenizer Polytron PT-3000 (Brinkmann Instruments, Westbury N.J.) in guanidinium isothiocyanate solution. The lysate was centrifuged over a 5.7 M CsCl cushion using a Beckman SW28 rotor in a Beckman L8-70M Ultracentrifuge (Beckman Instruments) for 18 hours at 25,000 rpm at ambient temperature. The RNA was extracted with phenol chloroform pH 4.0, precipitated using 0.3 M sodium acetate and 2.5 volumes of ethanol, resuspended in RNAse-free water and DNase treated at 37° C. The RNA was re-extracted with phenol chloroform pH 8.0 and precipitated using sodium acetate and ethanol as before. The mRNA was then isolated using the Qiagen Oligotex kit (QIAGEN Inc, Chatsworth, Calif.) and used to construct the cDNA library.

The mRNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. #275105; Pharmacia), and those cDNAs exceeding 400 bp were ligated into pSport I. The plasmid pSport I was subsequently transformed into DH5α™ competent cells (Cat. #18258-012; Gibco/BRL).

II Isolation and Sequencing of cDNA Clones

Plasmid DNA was released from the cells and purified using the REAL Prep 96 Plasmid Kit (Catalog #26173; QIAGEN Inc,). This kit enables the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES™, Gaithersburg, Md.) with carbenicillin at 25 mg/L and glycerol at 0.4%; 2) the cultures were incubated for 19 hours after the wells were inoculated and then lysed with 0.3 ml of lysis buffer; 3) following isopropanol precipitation, the plasmid DNA pellet was resuspended in 0.1 ml of distilled water. After the last step in the protocol, samples were transferred to a Beckman 96-well block for storage.

The cDNAs were sequenced by the method of Sanger F and A R Coulson (1975; J Mol Biol 94: 441 f), using a Hamilton Micro Lab 2200 (Hamilton, Reno NEV.) in combination with Peltier Thermal Cyclers (PTC200 from MJ Research, Watertown Mass.) and Applied Biosystems 377 DNA Sequencing Systems; and the reading frame was determined.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36: 290–300; Altschul et al. (1990) J. Mol. Biol. 215: 403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ® database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HPYP occurs. Abundance and percent abundance are also reported. Abundance directly reflects the number of times a particular transcript is represented in a cDNA library, and percent abundance is abundance divided by the total number of sequences examined in the cDNA library.

V Extension of HPYP-Encoding Polynucleotides to Full Length or to Recover Regulatory Sequences Full length HPYP-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK™ (QIAGEN Inc.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1xsaline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the HPYP-encoding sequence, or any part thereof, is used to inhibit in vivo or in vitro expression of naturally occurring HPYP. Although use of antisense oligonucleotides, comprising about 20 base-pairs, is specifically described, essentially the same procedure is used with larger cDNA fragments. An oligonucleotide based on the coding sequences of HPYP, as shown in FIGS. 1A, 1B, 1C and 1D is used to inhibit expression of naturally occurring HPYP. The complementary oligonucleotide is designed from the most unique 5' sequence as shown in FIGS. 1A, 1B, 1C and 1D and used either to inhibit transcription by preventing promoter binding to the up stream nontranslated sequence or translation of an HPYP-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A, 1B, 1C and 1D.

VIII Expression of HPYP

Expression of HPYP is accomplished by subcloning the cDNAs into appropriate vectors and transforming the vectors into host cells. In this case, the cloning vector, pSport, previously used for the generation of the DNA library is used to express HPYP in *E. coli*. upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HPYP into the bacterial growth media which can be used directly in the following assay for activity.

IX Demonstration of HPYP Activity

HPYP activity is measured by the hydrolysis of $^{32}$P-labeled PPi and quantitation of the recovered radioactivity using a gamma radioisotope counter. HPYP is incubated together with PPi in a PPase buffer containing 1–3 MM MgCl$_2$ and incubated at 37° C. for 10 minutes. PPi and Pi are then separated by polyethyleneimine cellulose thin layer chromatography in 1M KH$_2$PO$_4$ and the Pi fraction is isolated and counted. The radioactivity recovered is proportional to the enzyme activity.

X Production of HPYP Specific Antibodies

HPYP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HPYP Using Specific Antibodies

Naturally occurring or recombinant HPYP is substantially purified by immunoaffinity chromatography using antibodies specific for HPYP. An immunoaffinity column is constructed by covalently coupling HPYP antibody to an activated chromatographic resin, such as CnBr-activated Sepharose (Pharmacia & Upjohn). After the coupling, the resin is blocked and washed according to the manufacturer's instructions.

Media containing HPYP is passed over the immunoaffinity column, and the column is washed under conditions that allow the preferential absorbance of HPYP (e.g., high ionic strength buffers in the presence of detergent). The column is eluted under conditions that disrupt antibody/HPYP binding (eg, a buffer of pH 2–3 or a high concentration of a chaotrope, such as urea or thiocyanate ion), and HPYP is collected.

XII Identification of Molecules Which Interact with HPYP

HPYP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HPYP, washed and any wells with labeled HPYP complex are assayed. Data obtained using different concentrations of HPYP are used to calculate values for the number, affinity, and association of HPYP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. A purified human pyrophosphatase (HPYP) free of other human proteins, comprising the amino acid sequence of SEQ ID NO:1.

2. The HPYP of claim 1, wherein the HPYP is recombinantly produced.

3. The HPYP of claim 1, wherein the HPYP is synthetically produced.

4. The HPYP of claim 1, wherein the HPYP is joined to a polypeptide domain which facilitates purification of the HPYP.

5. A composition comprising the purified HPYP of claim 1 and an acceptable carrier.

* * * * *